(12) United States Patent
Gross

(10) Patent No.: US 8,414,559 B2
(45) Date of Patent: Apr. 9, 2013

(54) GASTRORETENTIVE DUODENAL PILL

(75) Inventor: Yossi Gross, Moshav Mazor (IL)

(73) Assignee: Rainbow Medical Ltd., Herzeliya (IL)

( * ) Notice: Subject to any disclaimer, the term of this patent is extended or adjusted under 35 U.S.C. 154(b) by 898 days.

(21) Appl. No.: 12/437,250

(22) Filed: May 7, 2009

(65) Prior Publication Data
US 2010/0286660 A1 Nov. 11, 2010

(51) Int. Cl.
*A61M 31/00* (2006.01)
(52) U.S. Cl.
USPC .......................................... 604/516; 604/523
(58) Field of Classification Search .......... 604/500–522, 604/8–10, 96.01, 523–53, 275, 536
See application file for complete search history.

(56) References Cited

U.S. PATENT DOCUMENTS

| | | | |
|---|---|---|---|
| 3,057,344 A | 10/1962 | Abella | |
| 3,118,439 A | 1/1964 | Perennoud | |
| 3,315,660 A | 4/1967 | Abella | |
| 3,485,235 A | 12/1969 | Ronald | |
| 3,659,600 A | 5/1972 | Merrill | |
| 4,239,040 A | 12/1980 | Hosoya et al. | |
| 4,315,509 A | 2/1982 | Smit | |
| 4,416,267 A | 11/1983 | Garren et al. | |
| 4,425,117 A | 1/1984 | Hugemann et al. | |
| 4,481,952 A * | 11/1984 | Pawelec | 600/582 |
| 4,507,115 A | 3/1985 | Kambara et al. | |
| 4,694,827 A | 9/1987 | Weiner et al. | |
| 4,723,547 A | 2/1988 | Kullas et al. | |
| 4,738,667 A | 4/1988 | Galloway | |
| 4,739,758 A | 4/1988 | Lai et al. | |
| 4,767,627 A | 8/1988 | Caldwell et al. | |
| 4,844,076 A | 7/1989 | Lesho et al. | |
| 4,869,248 A | 9/1989 | Narula | |
| 4,878,905 A | 11/1989 | Blass | |
| 4,899,747 A | 2/1990 | Garren et al. | |
| 4,959,485 A | 9/1990 | Youssefyeh et al. | |
| 4,987,136 A | 1/1991 | Kreek et al. | |

(Continued)

FOREIGN PATENT DOCUMENTS

EP 0246999 11/1987
WO WO 94/01165 1/1994

(Continued)

OTHER PUBLICATIONS

An International Search Report and a Written Opinion both dated Jul. 9, 2010 which issued during the prosecution of Applicant's PCT/IL10/00230.

(Continued)

*Primary Examiner* — Kevin C Sirmons
*Assistant Examiner* — Phillip Gray
(74) *Attorney, Agent, or Firm* — Husch Blackwell LLP

(57) ABSTRACT

Apparatus is provided that includes a swallowable medical treatment device, which is configured to initially assume a contracted state having a volume of less than 4 cm3. The device includes a gastric anchor, which initially assumes a contracted size, and which is configured to, upon coming in contact with a liquid, expand sufficiently to prevent passage of the anchor through a round opening having a diameter of between 1 cm and 3 cm. The device also includes a duodenal unit, which is configured to pass through the opening, and which is coupled to the gastric anchor such that the duodenal unit is held between 1 cm and 20 cm from the gastric anchor. Other embodiments are also described.

36 Claims, 4 Drawing Sheets

U.S. PATENT DOCUMENTS

| | | | |
|---|---|---|---|
| 5,019,034 A | 5/1991 | Weaver et al. |
| 5,052,998 A | 10/1991 | Zimmon |
| 5,129,915 A | 7/1992 | Cantenys |
| 5,167,626 A | 12/1992 | Casper et al. |
| 5,170,801 A | 12/1992 | Casper et al. |
| 5,188,104 A | 2/1993 | Wernicke et al. |
| 5,217,449 A | 6/1993 | Yuda et al. |
| 5,234,454 A | 8/1993 | Bangs |
| 5,263,480 A | 11/1993 | Wernicke et al. |
| 5,279,607 A | 1/1994 | Schentag et al. |
| 5,318,557 A | 6/1994 | Gross et al. |
| 5,320,598 A | 6/1994 | Haak et al. |
| 5,395,366 A | 3/1995 | D'Andrea et al. |
| 5,423,872 A | 6/1995 | Cigaina |
| 5,464,395 A | 11/1995 | Faxon et al. |
| 5,474,785 A | 12/1995 | Wright et al. |
| 5,536,274 A | 7/1996 | Neuss |
| 5,551,953 A | 9/1996 | Latin et al. |
| 5,604,531 A | 2/1997 | Iddan et al. |
| 5,674,196 A | 10/1997 | Donaldson et al. |
| 5,690,691 A | 11/1997 | Chen et al. |
| 5,738,110 A | 4/1998 | Beal et al. |
| 5,792,100 A | 8/1998 | Shantha |
| 5,792,203 A | 8/1998 | Schroeppel |
| 5,843,138 A | 12/1998 | Evers et al. |
| 5,868,141 A | 2/1999 | Ellias |
| 5,919,216 A | 7/1999 | Houben et al. |
| 5,925,030 A | 7/1999 | Gross et al. |
| 5,947,921 A | 9/1999 | Johnson et al. |
| 5,951,538 A | 9/1999 | Joshi et al. |
| 5,961,482 A | 10/1999 | Chien et al. |
| 5,964,726 A | 10/1999 | Korenstein et al. |
| 5,983,131 A | 11/1999 | Weaver et al. |
| 5,983,134 A | 11/1999 | Ostrow |
| 5,983,135 A | 11/1999 | Avrahami |
| 5,984,860 A | 11/1999 | Shan |
| 5,993,434 A | 11/1999 | Dev et al. |
| 6,002,961 A | 12/1999 | Mitragotri et al. |
| 6,018,678 A | 1/2000 | Mitragotri et al. |
| 6,024,717 A | 2/2000 | Ball et al. |
| 6,041,253 A | 3/2000 | Kost et al. |
| 6,070,103 A | 5/2000 | Ogden |
| 6,082,366 A | 7/2000 | Andra et al. |
| 6,090,095 A | 7/2000 | McNichols et al. |
| 6,091,872 A | 7/2000 | Katoot |
| 6,091,992 A | 7/2000 | Bourgeois et al. |
| 6,135,978 A | 10/2000 | Houben et al. |
| 6,148,232 A | 11/2000 | Avrahami |
| 6,175,763 B1 | 1/2001 | Sorenson et al. |
| 6,183,461 B1 | 2/2001 | Matsuura et al. |
| 6,190,315 B1 | 2/2001 | Kost et al. |
| 6,191,102 B1 | 2/2001 | Dlmarchi et al. |
| 6,219,576 B1 | 4/2001 | Gupta et al. |
| 6,234,990 B1 | 5/2001 | Rowe et al. |
| 6,235,313 B1 | 5/2001 | Mathiowitz et al. |
| 6,238,423 B1 | 5/2001 | Brady |
| 6,243,607 B1 | 6/2001 | Mintchev et al. |
| 6,245,057 B1 | 6/2001 | Sieben et al. |
| 6,246,904 B1 | 6/2001 | Murdock |
| 6,261,320 B1 | 7/2001 | Tam et al. |
| 6,322,532 B1 | 11/2001 | D'Sa et al. |
| 6,322,560 B1 | 11/2001 | Garbagnati et al. |
| 6,327,426 B1 | 12/2001 | Joshi et al. |
| 6,327,503 B1 | 12/2001 | Familoni |
| 6,344,027 B1 | 2/2002 | Goll et al. |
| 6,363,282 B1 | 3/2002 | Nichols et al. |
| 6,364,868 B1 | 4/2002 | Ikeguchi |
| 6,369,039 B1 | 4/2002 | Palasis et al. |
| 6,428,469 B1 | 8/2002 | Iddan et al. |
| 6,440,069 B1 | 8/2002 | Raymond et al. |
| 6,443,945 B1 | 9/2002 | Marchitto et al. |
| 6,453,199 B1 | 9/2002 | Kobozev |
| 6,454,785 B2 | 9/2002 | De Hoyos et al. |
| 6,464,687 B1 | 10/2002 | Ishikawa et al. |
| 6,471,696 B1 | 10/2002 | Berube et al. |
| 6,477,410 B1 | 11/2002 | Henley et al. |
| 6,491,657 B2 | 12/2002 | Rowe et al. |
| 6,535,764 B2 | 3/2003 | Imran et al. |
| 6,571,127 B1 | 5/2003 | Ben-Haim et al. |
| 6,572,740 B2 | 6/2003 | Rosenblum et al. |
| 6,575,969 B1 | 6/2003 | Rittman, III et al. |
| 6,579,301 B1 | 6/2003 | Bales et al. |
| 6,600,953 B2 | 7/2003 | Flesler et al. |
| 6,632,216 B2 | 10/2003 | Houzego et al. |
| 6,654,635 B1 | 11/2003 | Koga et al. |
| 6,656,194 B1 | 12/2003 | Gannoe et al. |
| 6,676,657 B2 | 1/2004 | Wood |
| 6,678,554 B1 | 1/2004 | Sun et al. |
| 6,684,105 B2 | 1/2004 | Cohen et al. |
| 6,685,962 B2 | 2/2004 | Friedman et al. |
| 6,692,456 B1 | 2/2004 | Eppstein et al. |
| 6,709,388 B1 | 3/2004 | Mosse et al. |
| 6,718,201 B1 | 4/2004 | Phipps et al. |
| 6,733,512 B2 | 5/2004 | McGhan |
| 6,743,198 B1 | 6/2004 | Tihon |
| 6,776,999 B1 | 8/2004 | Krumme |
| 6,826,428 B1 | 11/2004 | Chen et al. |
| 6,832,114 B1 | 12/2004 | Whitehurst et al. |
| 6,853,862 B1 | 2/2005 | Marchal et al. |
| 6,895,279 B2 | 5/2005 | Loeb et al. |
| 6,929,636 B1 | 8/2005 | Von Alten et al. |
| 6,947,791 B2 | 9/2005 | Zhang et al. |
| 6,951,536 B2 | 10/2005 | Yokoi et al. |
| 6,958,034 B2 | 10/2005 | Iddan |
| 6,993,391 B2 | 1/2006 | Flesler et al. |
| 6,994,095 B2 | 2/2006 | Burnett |
| 7,006,871 B1 | 2/2006 | Darvish et al. |
| 7,009,634 B2 | 3/2006 | Iddan |
| 7,033,384 B2 | 4/2006 | Gannoe et al. |
| 7,069,552 B2 | 6/2006 | Lindberg et al. |
| 7,160,258 B2 | 1/2007 | Imran et al. |
| 7,167,755 B2 | 1/2007 | Seeberger et al. |
| 7,267,694 B2 | 9/2007 | Levine et al. |
| 7,320,696 B2 | 1/2008 | Gazi et al. |
| 7,476,256 B2 | 1/2009 | Meade et al. |
| 2001/0035902 A1 | 11/2001 | Iddan et al. |
| 2002/0072779 A1 | 6/2002 | Loeb |
| 2002/0183682 A1 | 12/2002 | Darvish et al. |
| 2002/0183683 A1 | 12/2002 | Lerner |
| 2002/0198470 A1 | 12/2002 | Imran et al. |
| 2003/0021845 A1 | 1/2003 | Friedman et al. |
| 2003/0040696 A1 | 2/2003 | Mori et al. |
| 2003/0055464 A1 | 3/2003 | Darvish et al. |
| 2003/0055467 A1 | 3/2003 | Ben-Haim et al. |
| 2003/0093031 A1 | 5/2003 | Long et al. |
| 2003/0100040 A1 | 5/2003 | Bonnecaze et al. |
| 2003/0125788 A1 | 7/2003 | Long |
| 2003/0133976 A1 | 7/2003 | Pather et al. |
| 2003/0153866 A1 | 8/2003 | Long et al. |
| 2003/0158569 A1 | 8/2003 | Wazne |
| 2003/0167000 A1 | 9/2003 | Mullick et al. |
| 2003/0176892 A1 | 9/2003 | Shalev |
| 2003/0181958 A1 | 9/2003 | Dobak, III |
| 2003/0191492 A1 | 10/2003 | Gellman |
| 2004/0044357 A1 | 3/2004 | Gannoe et al. |
| 2004/0050394 A1 | 3/2004 | Jin |
| 2004/0088008 A1 | 5/2004 | Gannoe et al. |
| 2004/0088022 A1 | 5/2004 | Chen |
| 2004/0093091 A1 | 5/2004 | Gannoe et al. |
| 2004/0127942 A1 | 7/2004 | Tomtov et al. |
| 2004/0158288 A1 | 8/2004 | Keisari et al. |
| 2004/0162501 A1 | 8/2004 | Imran |
| 2004/0172088 A1 | 9/2004 | Knudson et al. |
| 2004/0176685 A1 | 9/2004 | Takizawa et al. |
| 2004/0176812 A1 | 9/2004 | Knudson |
| 2004/0180086 A1 | 9/2004 | Ramtoola et al. |
| 2004/0186530 A1 | 9/2004 | Gluschuk et al. |
| 2004/0249421 A1 | 12/2004 | Harel et al. |
| 2004/0253304 A1 | 12/2004 | Gross et al. |
| 2004/0267240 A1 | 12/2004 | Gross et al. |
| 2004/0267378 A1 | 12/2004 | Gazi et al. |
| 2005/0004430 A1 | 1/2005 | Lee et al. |
| 2005/0007232 A1 | 1/2005 | Ono et al. |
| 2005/0021101 A1 | 1/2005 | Chen et al. |
| 2005/0033331 A1 | 2/2005 | Burnett et al. |
| 2005/0055039 A1 | 3/2005 | Burnett et al. |
| 2005/0058701 A1 | 3/2005 | Gross et al. |

| | | |
|---|---|---|
| 2005/0085923 A1 | 4/2005 | Levine et al. |
| 2005/0096750 A1* | 5/2005 | Kagan et al. ............... 623/23.65 |
| 2005/0137633 A1 | 6/2005 | Salo et al. |
| 2005/0158246 A1 | 7/2005 | Takizawa et al. |
| 2005/0171563 A1 | 8/2005 | Heinrich et al. |
| 2005/0192614 A1 | 9/2005 | Binmoeller |
| 2005/0228504 A1 | 10/2005 | Demarais |
| 2006/0020278 A1 | 1/2006 | Burnett et al. |
| 2006/0069400 A1 | 3/2006 | Burnett et al. |
| 2006/0085045 A1 | 4/2006 | Harel et al. |
| 2006/0129205 A1 | 6/2006 | Boveja et al. |
| 2006/0142731 A1 | 6/2006 | Brooks |
| 2006/0178557 A1 | 8/2006 | Mintchev et al. |
| 2006/0190019 A1 | 8/2006 | Gannoe et al. |
| 2006/0276844 A1 | 12/2006 | Alon et al. |
| 2006/0287692 A1 | 12/2006 | Hall et al. |
| 2007/0005147 A1* | 1/2007 | Levine et al. ............. 623/23.65 |
| 2007/0016262 A1 | 1/2007 | Gross et al. |
| 2007/0060971 A1 | 3/2007 | Glaberg et al. |
| 2007/0156248 A1 | 7/2007 | Marco et al. |
| 2007/0250132 A1 | 10/2007 | Burnett |
| 2007/0293885 A1 | 12/2007 | Binmoeller |
| 2008/0063703 A1* | 3/2008 | Gross et al. .................... 424/463 |
| 2008/0065168 A1 | 3/2008 | Bitton et al. |
| 2008/0188837 A1 | 8/2008 | Belsky et al. |
| 2008/0234834 A1 | 9/2008 | Meade et al. |
| 2008/0275430 A1 | 11/2008 | Belsky et al. |
| 2008/0281375 A1 | 11/2008 | Chen |
| 2009/0030473 A1 | 1/2009 | Khawaled et al. |
| 2009/0062881 A1 | 3/2009 | Gross et al. |
| 2009/0171410 A1 | 7/2009 | Benarie et al. |
| 2009/0247992 A1 | 10/2009 | Shalon et al. |
| 2010/0021536 A1 | 1/2010 | Gross et al. |

FOREIGN PATENT DOCUMENTS

| | | |
|---|---|---|
| WO | WO 2004/089262 | 10/2004 |
| WO | WO 2005/009288 | 2/2005 |
| WO | WO 2005/039457 | 5/2005 |
| WO | WO 2006/047708 | 5/2006 |
| WO | WO 2006/064503 | 6/2006 |
| WO | WO 2007/007339 | 1/2007 |
| WO | WO 2008/023374 | 2/2008 |
| WO | WO 2008/121409 | 10/2008 |
| WO | WO 2008/121831 | 10/2008 |
| WO | WO 2008/154450 | 12/2008 |

OTHER PUBLICATIONS

An International Search Report and a Written Opinion both dated Nov. 23, 2011 which issued during the prosecution of Applicant's PCT/IL11/00433.

Klausner EA, et al., "Expandable gastroretentive dosage forms", Journal of Controlled Release 90:143-162, 2003.

Sun, et al., "Intestinal electric stimulation decreases fat absorption in rats: Therapeutic potential for obesity", Obes Res. Aug. 2004;12(8): 1235-42.

An Office Action dated Jun. 15, 2012, which issued during the prosecution of U.S. Appl. No. 12/793,978.

* cited by examiner

GASTRORETENTIVE DUODENAL PILL

FIELD OF THE INVENTION

The present invention relates generally to medical devices, and specifically to gastroretentive devices.

BACKGROUND OF THE INVENTION

Gastroretentive dosage forms (GRDFs) are swallowable drug delivery dosage forms having a prolonged gastric residence time, which substantially increases the time period during which the drug is released. Expandable GRDFs assume an initial, swallowable size, and expand in the stomach to a larger size that delays passage from the stomach.

Klausner E A et al., in "Expandable gastroretentive dosage forms," Journal of Controlled Release 90:143-162 (2003), which is incorporated herein by reference, survey expandable GRDFs as reported in articles and patents.

U.S. Pat. No. 6,776,999 to Krumme, which is incorporated herein by reference, describes a device for delaying the pylorus passage of orally administered medicament forms. The device comprises a component which expands upon contact with the gastric juice and a polymer coat which is permeable to liquids but not to gases. The device can contain an active substance whose release into the gastric juice is mainly controlled by the medicament form into which it is incorporated. The device can be easily rolled or folded and can be filled into capsules.

U.S. Pat. No. 4,767,627 to Caldwell et al., which is incorporated herein by reference, describes a drug delivery device retained in the stomach comprising a planar figure made from an erodible polymer that may release a drug associated therewith over a controlled, predictable and extended period of time.

U.S. Pat. No. 6,685,962 to Friedman et al., which is incorporated herein by reference, describes pharmaceutical gastroretentive drug delivery systems for the controlled release of an active agent in the gastrointestinal tract, which comprise: (a) a single- or multi-layered matrix comprising a polymer that does not retain in the stomach more than a conventional dosage form selected from (1) degradable polymers that may be hydrophilic polymers not instantly soluble in gastric fluids, enteric polymers substantially insoluble at pH less than 5.5 and/or hydrophobic polymers and mixtures thereof; (2) non-degradable polymers; and any mixtures of (1) and (2); (b) a continuous or non-continuous membrane comprising at least one polymer having a substantial mechanical strength; and (c) a drug; wherein the matrix when affixed or attached to the membrane prevents evacuation from the stomach of the delivery system for a period of time of between about 3 to about 24 hours.

US Patent Application Publication 2004/0180086 to Ramtoola et al., which is incorporated herein by reference, describes gastro-retentive dosage forms for prolonged delivery of levodopa and carbidopalevodopa combinations. The dosage forms comprise a tablet containing the active ingredient and a gas-generating agent sealed within an expandable, hydrophilic, water-permeable and substantially gas-impermeable membrane. Upon contact with gastric fluid, the membrane expands as a result of the release of gas from the gas-generating agent in the tablet. The expanded membrane is retained in the stomach for a prolonged period of time up to 24 hours or more during which period the active ingredient is released from the tablet providing delivery of levodopa to the site of optimum absorption in the upper small intestine.

U.S. Pat. No. 6,994,095 to Burnett, which is incorporated herein by reference, describes pyloric valve corking devices and methods. The devices generally include an occluding member which expands from a first configuration to a larger second configuration and a bridging member extending from the occluding member. The bridging member has a length which passes at least partially through the gastric opening such that the occluding member obstructs the gastric opening, and wherein the length permits the occluding member to intermittently move relative to the gastric opening. A second occluding member may be attached to the distal end of the bridging member. The reduction in flow of gastric contents into the duodenum can be tightly regulated using a pump or valve. Otherwise, the flow can be passively regulated with the occluding device.

PCT Publication WO 2008/121409 to Vargas, which is incorporated herein by reference, describes an intragastric implant comprising an anchor and a therapeutic device or a diagnostic device. The anchor is adapted to extend between the fundus and the pyloric valve of a stomach, to be retained without attachment to the stomach wall, and to anchor the device within the stomach with a relatively stable position and orientation. The therapeutic or diagnostic device is adapted to extend from the esophagus or stomach to the intestines or stomach. The therapeutic or diagnostic device, when extending into the esophagus, is slidably received through the gastroesophageal junction and, when extending into the intestines, is slidably received in the pyloric valve.

US Patent Application Publication 2007/0293885 to Binmoeller, which is incorporated herein by reference, describes an intestinal/duodenal insert comprising an elongated member with at least one flow reduction element that can cause the stimulation of one or more biological signals of satiety. Some embodiments of the inserted device are anchored at the duodenal site by an anchoring member residing in the stomach, while other embodiments of the device are stabilized at a targeted site by appropriate dimensions of length as well as one or more angled portions of the device that correspond to angled portions of the targeted site in the duodenum. Embodiments of the device exert effects by virtue of physical presence, as well as by more active forms of intervention, including release of bioactive materials and electrical stimulation of neurons.

PCT Publication WO 2008/154450 to Swain et al., which is incorporated herein by reference, describes techniques for attaching or maintaining the position of a therapeutic or diagnostic device in a body lumen, such as the GI tract, without necessarily requiring any penetrating attachments through any body walls. The system includes at least two elements: a proximal orientation element and a distal support element.

Gastric space fillers are known for filling a portion of the stomach, thereby reducing available space for food, and creating a feeling of satiety.

US Patent Application Publication 2007/0156248 to Marco et al., which is incorporated herein by reference, describes bioerodible, biodegradable, or digestible self-deploying intragastric implants that may be swallowed. Once swallowed, the implants undergo self-expansion in the stomach and apply a suitable pressure against the stomach wall to provide a feeling of satiety to the individual. The implants then dissolve or are disassembled perhaps using gastric liquids and pass out of the stomach.

PCT Publication WO 2008/121831 to Quijana et al., which is incorporated herein by reference, describes gastric space filler device for treating obesity in a patient by reducing the stomach volume features at least one inflatable space filler with drug delivery and stimulation features and includes therapeutic devices and anchoring apparatus enabling tracking, visualization and optimized management of inter-balloon connecting sections, drug reservoirs and pumping systems.

US Patent Application Publication 2006/0142731 to Brooks, which is incorporated herein by reference, describes a floating anchor, which can be inserted into the esophagus, stomach, small intestine, large intestine, or rectal cavity and reverts to a bent shape when placed therein.

PCT Publication WO 2008/023374 to Shalon et al., which is incorporated herein by reference, describes a device for modifying an eating behavior of a subject. The device includes a device body which is attachable to GI tract tissue of a subject and functions in altering an eating behavior thereof.

US Patent Application Publication 2007/0250132 to Burnett, which is incorporated herein by reference, describes techniques for applying gastrointestinal stimulation include implanting a stimulation device including a body with at least one expandable portion and a bridging portion and at least one stimulation member in the gastrointestinal tract. The at least one stimulation member includes one or more energy delivery members, one or more sensors, or a combination of both. The body maintains the device within the gastrointestinal space, and preferentially within the pyloric portion of the patient's stomach, and prevents passage of the device from the gastrointestinal space, but is not rigidly anchored or affixed to the gastrointestinal wall tissue.

PCT Publication WO 2007/007339 to Gross et al., which is incorporated herein by reference, describes a method including placing first and second electrodes at respective first and second sites of a duodenum of a subject, and activating the electrodes to increase a blood insulin level of the subject or to induce or increase a rate of peristalsis in the duodenum.

Sun et al., in "Intestinal electric stimulation decreases fat absorption in rats: Therapeutic potential for obesity," Obes Res. 2004 August; 12(8):1235-42, which is incorporated herein by reference, describe a study investigating whether intestinal electric stimulation (IES) would reduce fat absorption and, thus, would be a potential therapy for obesity.

U.S. Pat. No. 7,267,694 to Levine et al., which is incorporated herein by reference, describes techniques for limiting absorption of food products in specific parts of the digestive system. A gastrointestinal implant device is anchored in the stomach and extends beyond the ligament of Treitz. All food exiting the stomach is funneled through the device. The gastrointestinal device includes an anchor for anchoring the device to the stomach and a flexible sleeve to limit absorption of nutrients in the duodenum. The anchor is collapsible for endoscopic delivery and removal.

U.S. Pat. No. 7,476,256 to Meade et al., which is incorporated herein by reference, describes techniques for limiting absorption of food products in specific parts of the digestive system. A gastrointestinal implant device is anchored in the duodenum and extends beyond the ligament of Treitz. All food exiting the stomach is funneled through the device. The gastrointestinal device includes an anchor for attaching the device to the duodenum and an unsupported flexible sleeve to limit absorption of nutrients in the duodenum. The anchor can include a stent and/or a wave anchor and is collapsible for catheter-based delivery and removal.

US Patent Application Publication 2008/0234834 to Meade et al., which is incorporated herein by reference, describes a gastrointestinal implant device that includes a flexible, floppy sleeve, open at both ends, that extends into the duodenum. The device further includes a collapsible anchor coupled to the proximal portion of the sleeve. The device further includes a drawstring that is threaded through a proximal end of the anchor, and barbs that extend from the exterior surface of the anchor. The collapsible anchor can be a wave anchor. The drawstring can be used to collapse at least a proximal portion of the implant device. This is useful in removing or repositioning the implant device.

PCT Publication WO 06/064503 to Belsky et al., which is incorporated herein by reference, describes apparatus for drug administration, including an ingestible capsule, which includes a drug, stored by the capsule. The apparatus also includes an environmentally-sensitive mechanism, adapted to change a state thereof responsively to a disposition of the capsule within a gastrointestinal (GI) tract of a subject; one or more drug-passage facilitation electrodes; and a control component, adapted to facilitate passage of the drug, in response to a change of state of the environmentally-sensitive mechanism, by driving the drug-passage facilitation electrodes to apply an electrical current. The apparatus further includes a velocity-reduction element adapted to reduce a velocity of the capsule through the GI tract for at least a portion of the time that the control component is facilitating the passage of the drug.

PCT Publication WO/1994/001165 to Gross, which is incorporated herein by reference, describes a medication administering device that includes a housing introducible into a body cavity and of a material insoluble in the body cavity fluids, but formed with an opening covered by a material which is soluble in body cavity fluids. A diaphragm divides the interior of the housing into a medication chamber including the opening, and a control chamber. An electrolytic cell in the control chamber generates a gas when electrical current is passed therethrough to deliver medication from the medication chamber through the opening into the body cavity at a rate controlled by the electrical current. The device can be in the form of a pill or capsule to be taken orally.

U.S. Pat. No. 5,188,104 to Wernicke et al., which is incorporated herein by reference, describes a method for treating patients with compulsive eating disorders, including the steps of detecting a preselected event indicative of an imminent need for treatment of the specific eating disorder of interest, and responding to the detected occurrence of the preselected event by applying a predetermined stimulating signal to the patient's vagus nerve appropriate to alleviate the effect of the eating disorder of interest. For example, the preselected event may be a specified level of food consumption by the patient within a set interval of time, or the commencement of a customary mealtime according to the patient's circadian cycle, or the passage of each of a sequence of preset intervals of time, or the patient's own recognition of the need for treatment by voluntarily initiating the application of the stimulating signal to the vagus nerve. In cases in which the disorder is compulsive eating to excess, the stimulating signal is predetermined to produce a sensation of satiety in the patient. The occurrence of the preselected event is detected by summing the number of swallows of food by the patient within the set interval of time. In cases where the disorder is compulsive refusal to eat (anorexia nervosa), the stimulating signal is predetermined to produce a sensation of hunger or to suppress satiety in the patient.

SUMMARY OF THE INVENTION

In embodiments of the present invention, a swallowable treatment device comprises a gastric anchor coupled to a duodenal unit configured to reside in the duodenum. The gastric anchor initially assumes a contracted swallowable configuration. After being swallowed and entering the stomach, the anchor expands to prevent passage of the anchor through the pylorus even when the pylorus is in an open, relaxed state. The duodenal unit passes into the duodenum and is prevented by the gastric anchor from passing further into the gastrointestinal (GI) tract. At least a portion of the anchor eventually biodegrades in the stomach, causing the anchor to break down, and the entire device to be evacuated through the GI tract by peristalsis. For some applications, the treatment device further comprises a tether which couples the duodenal unit to the gastric anchor.

In some embodiments of the present invention, the gastric anchor comprises a flexible sheet sized to prevent passage of the anchor through the pylorus. The sheet is typically shaped so as to define a hole therethrough, through which chyme can pass to the pylorus and the duodenum. Before the device is swallowed, the sheet is rolled to assume a contracted swallowable configuration. Upon arriving in the stomach, the sheet unrolls and becomes positioned in the antrum of the stomach by gastric peristalsis. For some applications, the sheet is initially rolled around at least a portion of the duodenal unit.

In some embodiments of the present invention, the duodenal unit comprises a drug. For some applications, the duodenal unit comprises a conventional drug pill comprising the drug. The pill may comprise, for example, a capsule. Alternatively, the duodenal unit may comprise a slow-release reservoir that slowly releases the drug into the duodenum.

In some embodiments of the present invention, the duodenal unit comprises two or more duodenal stimulation electrodes that are configured to come in physical contact with the wall of at least a portion of the duodenum. The treatment device comprises a power source, such as a battery, and circuitry that is configured to drive the electrodes to apply an electrical current to the wall of the duodenum, and to configure the current to induce and/or increase a rate of peristalsis in the duodenum, and/or induce migrating motor complex (MMC) in the duodenum. As a result, the residence time of absorbable food calories in the duodenum is reduced. For some applications, the duodenal unit is shaped so as to define a passage therethrough, through which chyme can pass.

In some embodiments of the present invention, the duodenal unit comprises a bariatric sleeve sized to allow chyme to pass therethrough without coming into contact with the wall of at least a portion of the duodenum. Such bypassing of the duodenum reduces absorption of nutrients and calories. Optionally, the sleeve is long enough to additionally bypass a portion of the jejunum. The sleeve is typically biodegradable, such that after a period of time the sleeve degrades and is evacuated through the GI tract by peristalsis. The sleeve is typically coupled directly to the anchor, so that in these embodiments the tether is typically not provided. For some applications, the duodenal unit is initially shaped to have a rounded tip, which facilitates passage through the pylorus.

For some applications, the duodenal unit implements two or more of these techniques. For example, the unit may comprise both the drug and the duodenal stimulation electrodes.

There is therefore provided, in accordance with an embodiment of the present invention, apparatus including a swallowable medical treatment device, which is configured to initially assume a contracted state having a volume of less than 4 cm3, and which includes:

a gastric anchor, which initially assumes a contracted size, and which is configured to, upon coming in contact with a liquid, expand sufficiently to prevent passage of the anchor through a round opening having a diameter of between 1 cm and 3 cm; and a duodenal unit, which is configured to pass through the opening, and which is coupled to the gastric anchor such that the duodenal unit is held between 1 cm and 20 cm from the gastric anchor.

For some applications, the duodenal unit is coupled to the gastric anchor such that the duodenal unit is held between 2 cm and 5 cm from the gastric anchor.

For some applications, the apparatus further includes a dissolvable enclosure that entirely surrounds the swallowable medical treatment device when the device initially assumes the contracted state.

In an embodiment of the present invention, the apparatus further includes a tether, which couples the duodenal unit to the gastric anchor, and has a length of between 1 cm and 20 cm.

In an embodiment, the duodenal unit includes a drug. Alternatively or additionally, the duodenal unit includes two or more duodenal stimulation electrodes that are configured to come in physical contact with a wall of the duodenum, and the treatment device further includes a power source and circuitry that is configured to drive the electrodes to apply an electrical current to the wall of the duodenum.

In an embodiment, the duodenal unit includes a bariatric sleeve sized to allow chyme to pass therethrough without coming into contact with a wall of at least a portion of the duodenum.

In an embodiment, the gastric anchor includes a flexible sheet which initially is rolled around at least a portion of the duodenal unit to assume the contracted size, and which is configured to prevent the passage of the anchor through the opening by unrolling upon coming in contact with the liquid.

In an embodiment, the gastric anchor includes a flexible sheet which initially is rolled to assume the contracted size, and which is configured to prevent passage of the anchor through the opening by unrolling upon coming in contact with the liquid, which flexible sheet is shaped so as to define a hole therethrough having a radius of at least 0.4 cm.

In an embodiment, the opening is a pylorus of a subject, the liquid is stomach contents of the subject, the gastric anchor is configured to, upon coming in contact with the stomach contents, expand sufficiently to prevent passage of the anchor through the pylorus, and the duodenal unit is configured to pass through the pylorus, and is coupled to the gastric anchor such that the duodenal unit is held in a duodenum of the subject. For some applications, the gastric anchor is configured to at least partially biodegrade in a stomach of a subject, so as to allow passage of the anchor through the pylorus after a period of time.

There is further provided, in accordance with an embodiment of the present invention, apparatus including a swallowable medical treatment device, which is configured to initially assume a swallowable contracted state, and which includes:

a gastric anchor, which initially assumes a contracted size, and which is configured to, upon coming in contact with stomach contents of a subject, expand sufficiently to prevent passage of the anchor through a pylorus of the subject even when the pylorus is in an open, relaxed state; and a duodenal unit, which is configured to pass through the pylorus into a duodenum of the subject, and which is coupled to the gastric anchor such that the duodenal unit is held in the duodenum.

For some applications, the apparatus further includes a dissolvable enclosure that entirely surrounds the swallowable medical treatment device when the device initially assumes the swallowable contracted state.

In an embodiment, the apparatus further includes a tether, which couples the duodenal unit to the gastric anchor, and has a length of between 1 cm and 20 cm.

There is still further provided, in accordance with an embodiment of the present invention, apparatus including a swallowable medical treatment device, which is configured to initially assume a contracted state having a volume of less than 4 cm3, which includes:

a gastric anchor, which includes a flexible sheet which initially is rolled to assume a contracted size, which is configured to, upon coming in contact with a liquid, unroll to assume an expanded size that is sufficient to prevent passage of the anchor through a round opening having a diameter of between 1 cm and 3 cm, and which is shaped so as to define a hole therethrough having a radius of at least 0.4 cm; and a medical treatment component, which is coupled to the gastric anchor.

In an embodiment, the treatment component includes a drug. Alternatively or additionally, the treatment component includes an electrical stimulator. Alternatively, the treatment component includes a bariatric sleeve.

In an embodiment, the opening is a pylorus of a subject, the liquid is stomach contents of the subject, the gastric anchor is configured to, upon coming in contact with the stomach contents, unroll to assume the expanded size that is sufficient to prevent passage of the anchor through the pylorus, and the hole is sized to allow chyme to pass to the pylorus.

There is additionally provided, in accordance with an embodiment of the present invention, a method including:

receiving, by a subject, a swallowable medical treatment device in an initially contracted state, which device includes a gastric anchor having an initially contracted size, and a duodenal unit coupled to the gastric anchor; and swallowing the treatment device by the subject, so that the anchor, upon coming in contact with stomach contents of the subject, expands sufficiently to prevent passage of the anchor through a pylorus of the subject, and the duodenal unit passes through the pylorus into a duodenum of the subject and is held in the duodenum by the anchor.

There is yet additionally provided, in accordance with an embodiment of the present invention, a method including:

receiving, by a subject, a swallowable treatment device in an initially contracted state, which includes (i) a gastric anchor, which includes a flexible sheet which initially is rolled to assume a contracted size, and which is shaped so as to define an hole therethrough having a radius of at least 0.4 cm, and (ii) a treatment component coupled to the gastric anchor; and swallowing the treatment device by the subject, so that the anchor, upon coming in contact with stomach contents of the subject, unrolls sufficiently to prevent passage of the anchor through a pylorus of the subject, and to allow chyme to pass through the hole to the pylorus.

The present invention will be more fully understood from the following detailed description of embodiments thereof, taken together with the drawings, in which:

DETAILED DESCRIPTION OF EMBODIMENTS

Figure 1:
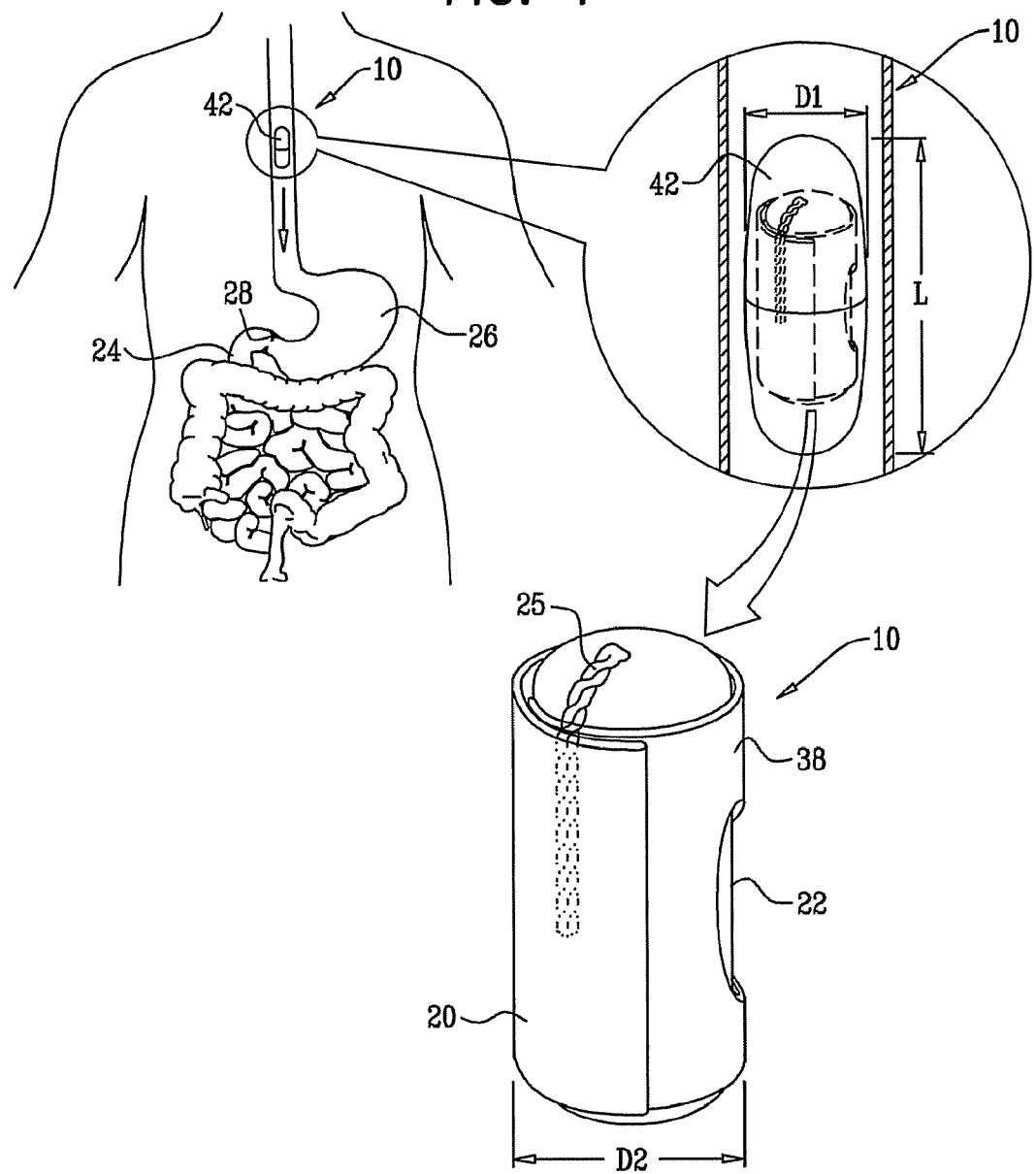
FIG. 1 is a schematic illustration of a swallowable medical treatment device in an initial contracted swallowable state, in accordance with an embodiment of the present invention.

FIG. 1 is a schematic illustration of a swallowable medical treatment device 10 in an initial contracted swallowable state, in accordance with an embodiment of the present invention. Treatment device 10 comprises a gastric anchor 20, and, coupled to the anchor, a duodenal unit 22 configured to reside in a duodenum 24 of a subject. For some applications, the treatment device further comprises a tether 25 that couples the anchor to the duodenal unit.

Gastric anchor 20 initially assumes a contracted swallowable state, as shown in FIG. 1. In this configuration, treatment device 10 typically has a total volume (including enclosure 42, if provided, as described hereinbelow) of less than about 4 cm3, such as less than about 3 cm3, to readily allow swallowing by the subject. For some applications, when in the initial, contracted swallowable configuration, treatment device 10 has an outer diameter D1 (including enclosure 42, if provided, as described hereinbelow) of less than 15 mm, e.g., between about 7 and about 13 mm, and/or a total length L of less than 35 mm, such as between about 8 and about 30 mm.

Figure 2:
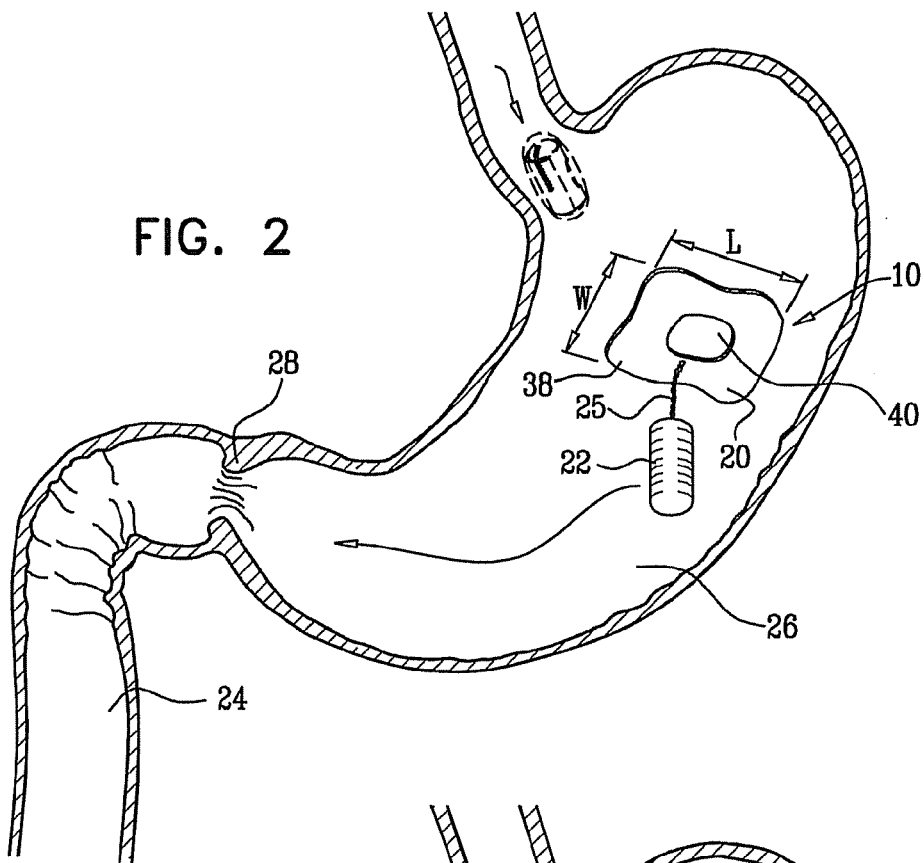
FIG. 2 is a schematic illustration of the medical treatment device of FIG. 1 in an expanded state in a stomach of a subject, in accordance with an embodiment of the present invention.

FIG. 2 is a schematic illustration of treatment device 10 in an expanded state in a stomach 26 of the subject, in accordance with an embodiment of the present invention. After being swallowed, entering stomach 26, and coming in contact with stomach contents, anchor 20 expands, such as by unrolling, to prevent passage of the anchor through a pylorus 28 even when the pylorus is in an open, relaxed state. More generally, anchor 20 is configured to initially assume a contracted size, and, upon coming in contact with a liquid, to expand sufficiently to prevent passage of the anchor through a round opening having a diameter of between 1 cm and 3 cm. Alternatively, anchor 20 is anchored in the stomach using a technique other than expansion.

Figure 3:
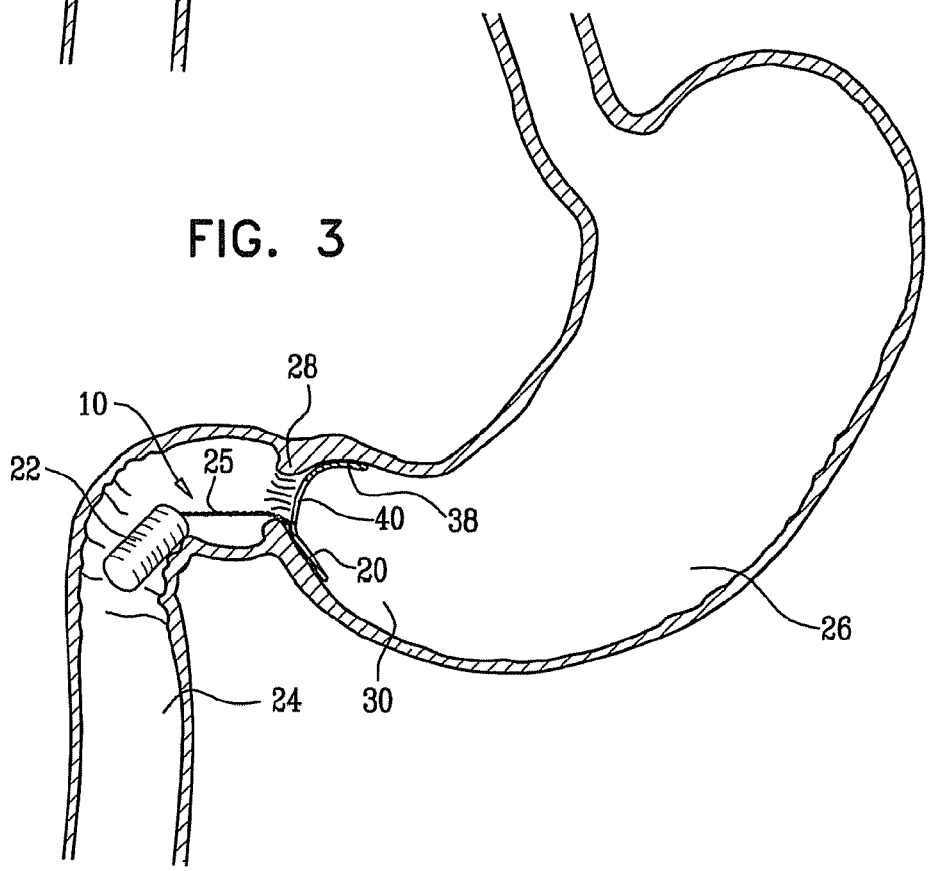
FIG. 3 is a schematic illustration of the medical treatment device of FIG. 1 in an anchored position, in accordance with an embodiment of the present invention.

FIG. 3 is a schematic illustration of treatment device 10 in an anchored position, in accordance with an embodiment of the present invention. After anchor 20 expands, gastric peristalsis positions treatment device 10 in an antrum 30 of stomach 26 in a vicinity of pylorus 28. Duodenal unit 22 passes into duodenum 24 and is held by anchor 20 from passing further into the gastrointestinal (GI) tract. Typically, the duodenal unit is coupled to the gastric anchor such that the duodenal unit is held within about 1 cm to about 20 cm of the gastric anchor, such as within about 5 cm of the gastric anchor, e.g., within 2-5 cm of the gastric anchor. For applications in which treatment device 10 comprises tether 25, the tether holds duodenal unit 22 from passing further into the GI tract. Typically, the tether has a length of between about 1 cm and about 20 cm, such as between about 2 cm and about 5 cm, such that duodenal unit 22 is held in duodenum 24.

At least a portion of anchor 20 eventually biodegrades in the stomach, causing the anchor to break down or break apart into smaller pieces, and the entire device to be evacuated through the GI tract by peristalsis (not shown). For some applications, the anchor is configured to biodegrade between about 1 and about 24 hours after the device is swallowed, such as between about 1 and about 8 hours after the device is swallowed.

In an embodiment of the present invention, gastric anchor 20 comprises a flexible sheet 38 sized to prevent passage of the anchor through the pylorus, as shown in FIGS. 1-3. Sheet 38 typically is shaped so as to define a hole 40 therethrough (e.g., a central hole), through which chyme can pass to the pylorus and the duodenum. The hole is larger than the opening of pylorus 28 when open, and large enough to allow passage through hole 40 of duodenal unit 22. Typically, the hole has a radius of between about 0.25 and about 2 cm, such as between about 0.5 and about 1 cm. Before the device is swallowed, sheet 38 is rolled to assume a contracted, swallowable size, as shown in FIG. 1. Upon arriving in the stomach, as shown in FIG. 2, the sheet unrolls and is positioned in antrum 30 by gastric peristalsis, as shown in FIG. 3. (The duodenal unit sometimes passes through the pylorus before the anchor settles near the pylorus, and sometimes passes through hole 40 after the anchor settles near the pylorus.)

For some applications, sheet 38 is initially rolled around at least a portion of the duodenal unit, as shown in FIG. 1. Alternatively, the sheet is initially positioned longitudinally or laterally adjacent to duodenal unit 22, and the sheet and unit are removably coupled to one another, such that they come decoupled upon exposure to the contents of the stomach (configurations not shown). Further alternatively, the sheet and duodenal unit are initially coupled together only by tether 25 (configuration not shown). For some applications, the sheet is initially held in the rolled position by one or more dissolvable elements, such as one or more dissolvable rings placed around the rolled sheet (e.g., comprising gelatin), or a dissolvable glue that binds the outermost edge of the sheet to a more inner portion of the sheet. These dissolvable elements dissolve once the device reaches stomach 26. Alternatively or additionally, the sheet is initially held in the rolled position by a dissolvable capsule or coating, as described hereinbelow.

For some applications, sheet 38 has a length L of between about 20 and about 40 mm, such as about 25 mm, and a width of between about 10 and about 30 mm, such as about 25 mm, as indicated in FIG. 2. Typically, the width of sheet 38 is approximately equal to the length of duodenal unit 22. For some applications, when the sheet assumes its initial rolled position, as shown in FIG. 1, the sheet has an outer diameter D2 of between about 10 and about 20 mm.

For some applications in which anchor 20 comprises sheet 38 defining hole 40, treatment device 10 does not comprise duodenal unit 22. Instead, the anchor is coupled to another medical treatment component that remains in the stomach with the anchor. For example, the treatment component may comprise a drug (e.g., a slow-release drug), an electrical stimulator configured to apply electrical stimulation to the stomach, or both the drug and the electrical stimulator. For example, the electrical stimulator may apply the electrical stimulation at between 5 and 7 mA, at a frequency of between 5 and 40 Hz (e.g., 30 Hz), optionally in pulse trains (e.g., 5 second on periods alternating with 2.5 second off periods), for example to generate peristalsis.

Alternatively, gastric anchor 20 uses other chemical and/or mechanical techniques for expansion. For example, the anchor may comprise a material that swells upon contact with the liquid contents of the stomach. Alternatively, the anchor may comprise one or more mechanical elements that are initially held in a compressed position, and expand, e.g., unfold, upon being released when the device reaches the stomach. For some applications, expansion techniques are used that are described in the above-mentioned article by Klausner EA et al. and/or the other references incorporated herein by reference in the Background section.

For some applications, treatment device 10 comprises a dissolvable enclosure 42 that entirely surrounds device 10 when the device initially assumes its contracted swallowable state, thereby encapsulating or coating the device, such as shown in FIG. 1. For example, dissolvable enclosure 42 may comprise a hard- or soft-shelled capsule or coating, e.g., comprising gelatin or another water-soluble material. The enclosure facilitates safe and easy swallowing of the device, and dissolves once the device reaches stomach 26. In addition, the enclosure may help prevent expansion of the device before it reaches the stomach.

In some embodiments of the present invention, the duodenal unit comprises a drug. For some applications, the duodenal unit comprises a conventional drug pill comprising the drug. The pill may comprise, for example, a capsule. Alternatively, the duodenal unit may comprise a slow-release reservoir that slowly releases the drug into the duodenum. For some applications, anchor 20 is alternatively or additionally coated with a drug (either the same drug as or a different drug from that of the duodenal unit).

Figure 4:
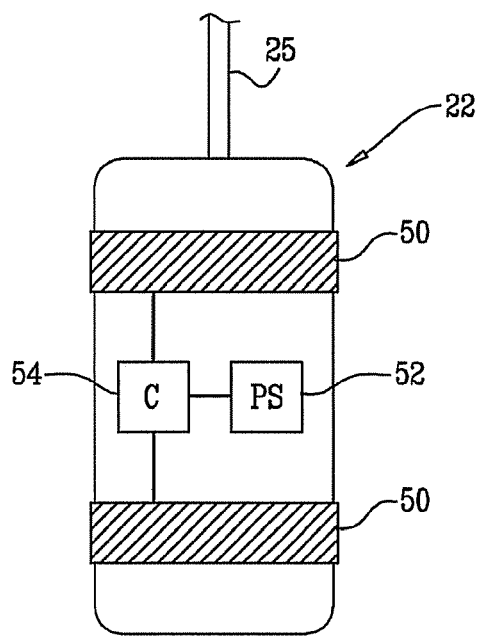
FIGS. 4 and 5 are schematic illustrations of an electrical stimulation duodenal unit of the medical treatment device of FIG. 1, in accordance with respective embodiments of the present invention.

Reference is made to FIG. 4, which is a schematic illustration of an electrical stimulation embodiment of duodenal unit 22, in accordance with an embodiment of the present invention. In this embodiment, duodenal unit 22 comprises two or more duodenal stimulation electrodes 50 that are configured to come in physical contact with the wall of duodenum 24. For some applications, one or more of the electrodes wrap around the outer surface of the duodenal unit, as shown in FIG. 4. Alternatively or additionally, one or more of the electrodes are oriented along the length of the duodenal unit (configuration not shown). The treatment device comprises a power source 52, such as a battery, and circuitry 54 that is configured to drive electrodes 50 to apply an electrical current to the wall of the duodenum.

In an embodiment of the present invention, circuitry 54 configures the current to induce and/or increase a rate of peristalsis in the duodenum, and/or induce migrating motor complex (MMC) in the duodenum. As a result, the residence time of absorbable food calories in the duodenum is reduced, as is glucose uptake and other forms of calorie uptake.

In an embodiment of the present invention, circuitry 54 is configured to stimulate the vagus nerve, thereby generating satiety-related signals that travel to the brain and cause satiety (see, for example, the above-mentioned U.S. Pat. No. 5,188,104 to Wernicke et al., which describes vagal stimulation techniques for inducing satiety). For example, parameters described in the following paragraph may be used for stimulating the vagus nerve. For some applications, tether 25 has a length of up to 10 cm, which holds duodenal unit 22 in the duodenum near the pylorus near a branch of the vagus nerve.

For some applications, circuitry 54 configures the current to have an amplitude of between 2 and 10 mA, e.g., between 4 and 6 mA, such as 5 mA. For some applications, circuitry 54 applies the current in a series of pulses, each of which has a duration of between 0.1 and 10 milliseconds, e.g., between 0.5 and 2 milliseconds (such as 1 millisecond), or between 2 and 7 milliseconds (such as 5 milliseconds). For some applications, circuitry 54 applies the current in a plurality of series of pulses, which series are separated by periods during which the current is not applied. For some applications, the circuitry applies the pulses at a frequency of between 10 and 100 Hz, such as between 15 and 30 Hz (e.g., 20 Hz), between 25 and 75 Hz (e.g., 50 Hz), or between 75 and 125 Hz (e.g., 100 Hz). For some applications, circuitry 54 applies the current intermittently during stimulation periods alternating with non-stimulation periods. For example, the stimulation periods may have a duration of about an hour, and the non-stimulations periods may have a duration of about 30 minutes, and the device may apply stimulation for a total of about 8 hours until the device biodegrades. For some applications, the circuitry applies the pulses as square pulses. For some applications, the circuitry configures the pulses to be biphasic (e.g., each phase may have a duration equal to half of the pulse duration). For some applications, the circuitry applies the pulses in a train, e.g., having "on" periods (e.g., each of which having a duration of about two seconds) alternating with "off" periods (e.g., each of which having a duration of between about 3 and about 8 seconds).

In an embodiment of the present invention, circuitry 54 is configured to intermittently drive electrodes 50 to apply the current. For example, the circuitry may drive the electrodes to apply the current during activation periods each of which has a duration of between about five and about fifteen minutes (e.g., about ten minutes), alternating with non-stimulation periods each of which has a duration of between about 30 and about 60 minutes.

For some applications, circuitry 54 is configured to wait a certain period of time after the duodenal unit enters the duodenum before driving the electrodes to induce peristalsis, thereby allowing time for food to enter the duodenum from the stomach. The subject may swallow treatment device 10 before beginning a meal. As appropriate, techniques described in the above-cited article to Sun et al. may be adapted for use in this embodiment for stimulating the duodenum.

For some applications, duodenal unit 22 comprises power source 52 and/or circuitry 54, while for other applications, gastric anchor 20 comprises the power source and/or circuitry, in which case tether 25 may comprise one or more wires to convey the current to the duodenal unit, or the device is configured to wirelessly transmit power from the anchor to the duodenal unit. For some applications, duodenal unit 22 comprises a coating, such as an enteric coating.

Figure 5:
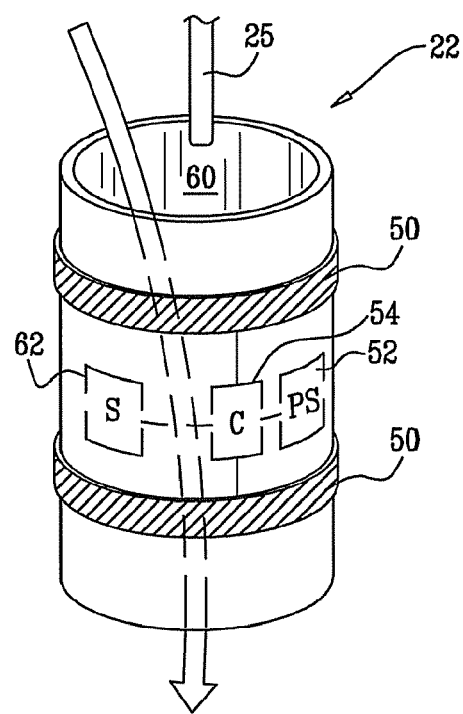

FIG. 5 is a schematic illustration of another configuration of duodenal unit 22, in accordance with an embodiment of the present invention. Other than as described below, this configuration is similar to the configuration described hereinabove with reference to FIG. 4. In this configuration, the duodenal unit is shaped so as to define a passage 60 therethrough, through which chyme can pass. For some applications, the duodenal unit is flexible, in order to accommodate peristaltic waves of the duodenum. For some applications, the gastric anchor is initially rolled up inside passage 60 of the duodenal unit.

For some applications, duodenal unit 22 comprises a sensor 62, which is configured to detect the passage of chyme through passage 60 or past the unit (such as for applications in which the unit is not shaped so as to define passage 60), and/or opening of pylorus 28. Circuitry 54 is configured to drive electrodes 50 to apply the current responsively to detection of chyme passage by the sensor (e.g., upon detection, or a certain amount of time after detection), and to cease driving the electrodes when chyme passage is no longer detected or the pylorus closes, or after a certain period of time. This regulated application of current may conserve power, and/or avoid any undesirable effects of excessive electrical stimulation of the duodenum. For some applications, sensor 62 detects opening of the pylorus by electromyographic (EMG) analysis of physiological electrical activity sensed by an electrode on the pylorus. Techniques for identifying a change in state of a muscle using EMG analysis are known in the art. Alternatively, other sensors adapted to sense pyloric opening and closing may be used, such as an acceleration sensor, a strain gauge, or an ultrasound sensor.

Alternatively or additionally, induction of the peristalsis or MMC is initiated in response to a detection of the occurrence of segmentation of the duodenum; the induced peristalsis or MMC typically terminates the segmentation process. For some applications, segmentation is detected responsively to a pattern of electrical activity along the duodenum that is measured by electrodes 50 and analyzed by circuitry 54. Alternatively, induction of the peristalsis or MMC is practiced not in response to any sensed event. For example, the peristalsis or MMC may be artificially initiated for a certain amount of time during one or more periods every day. For some applications, induction of the peristalsis or MMC is not performed when the subject is asleep.

Alternatively or additionally, treatment device 10 (either gastric anchor 20 or duodenal unit 22) comprises an eating sensor (e.g., a swallowing sensor), which is configured to generate a signal indicative of eating by the subject. Circuitry 54 is configured to drive electrodes 50 to apply the current responsively to the sensing of eating. Alternatively, the circuitry drives the electrodes to apply the current not responsively to sensing of eating.

For some applications, at least a portion of duodenal unit 22 is biodegradable, such that the duodenal unit eventually breaks down and is evacuated through the GI tract by peristalsis. Alternatively, the duodenal unit is not configured to be biodegradable, and is evacuated intact through the GI tract by peristalsis when anchor 20 breaks down, as described hereinabove with reference to FIG. 3.

Figure 6:
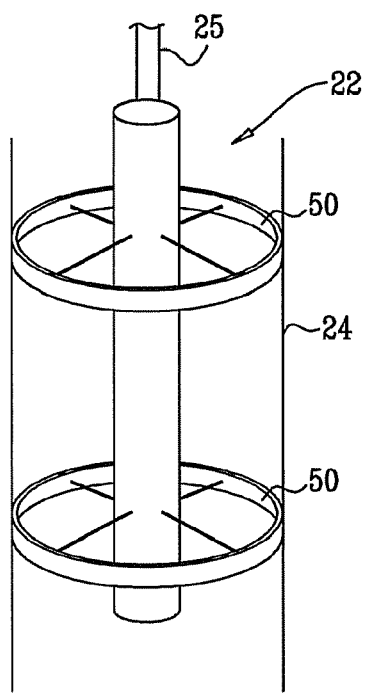
FIG. 6 is a schematic illustration of a configuration of the duodenal unit of the medical treatment device of FIG. 1 including expandable electrodes, in accordance with an embodiment of the present invention.

FIG. 6 is a schematic illustration of a configuration of duodenal unit 22 in which electrodes 50 are expandable, in accordance with an embodiment of the present invention. In this configuration, electrodes 50 are configured to expand to come in contact with the wall of duodenum 24, such as by elastic components, e.g., springs. Typically, the diameter of the body of duodenal unit 22 is sized to allow chyme to pass between the body and the duodenal wall.

In an embodiment of the present invention, device 10 does not comprise gastric anchor 20 or tether 25. Instead, electrical stimulation duodenal unit 22 comprises a mucoadhesive applied to an external surface of the unit. The mucoadhesive causes the unit to adhere partially or completely to the wall of the duodenum, thereby slowing down or stopping motion of the unit in the duodenum for a period of time. For some applications, the unit comprises an enteric coating that coats the mucoadhesive, and is configured to dissolve in the duodenum, thereby preserving the mucoadhesive until the unit arrives in the duodenum.

Figure 7:
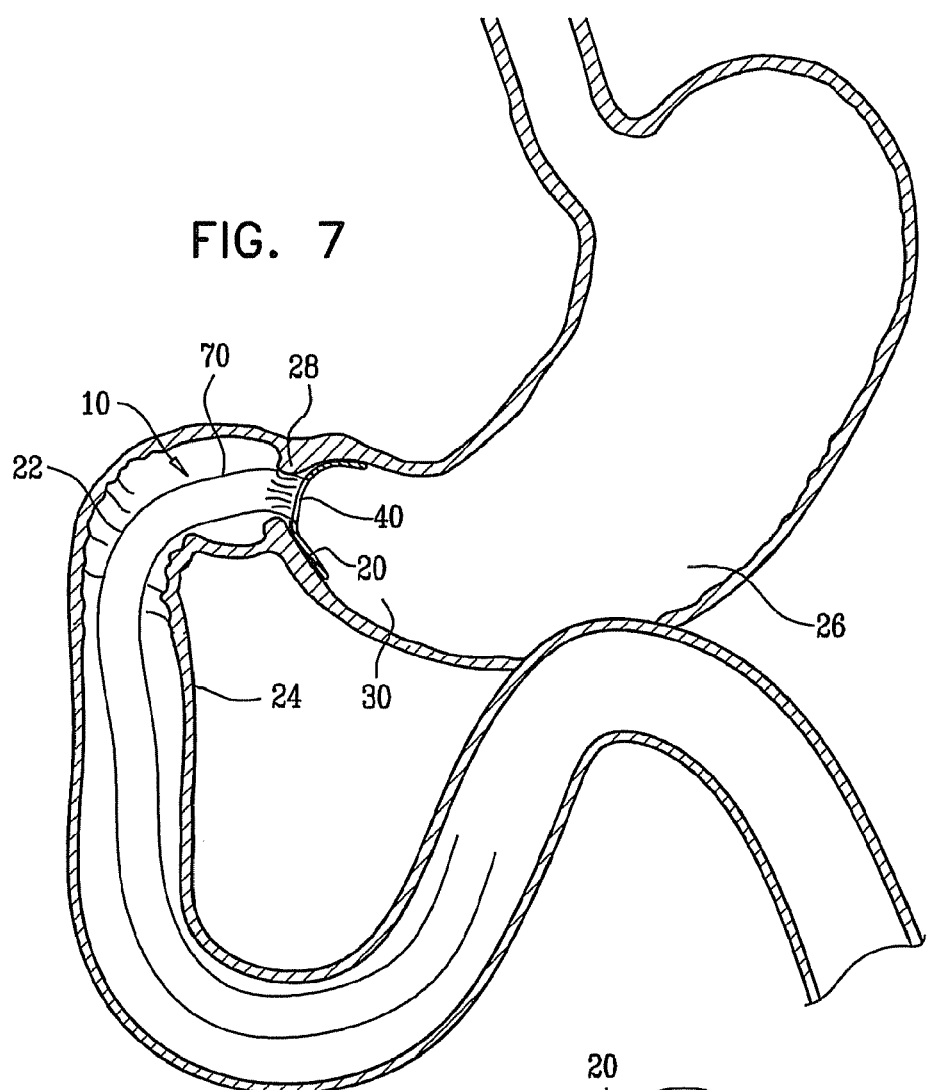
FIG. 7 is a schematic illustration of a bariatric sleeve duodenal unit of the medical treatment device of FIG. 1, in accordance with an embodiment of the present invention.

Reference is made to FIG. 7, which is a schematic illustration of an embodiment in which duodenal unit 22 comprises a bariatric sleeve 70, in accordance with an embodiment of the present invention. Bariatric sleeve 70 is sized to allow chyme to pass therethrough without coming into contact with the wall of at least a portion of duodenum 24. Such bypassing of the duodenum reduces absorption of nutrients and calories. Optionally, the sleeve is long enough to additionally bypass a portion of the jejunum. The sleeve is typically biodegradable, such that after a period of time the sleeve degrades and is evacuated through the GI tract by peristalsis. The length of the sleeve is typically between about 5 cm and about 30 cm, and may be selected for each subject depending upon the weight loss that is desired to be induced by the sleeve. The diameter of the sleeve is typically between about 10 and about 30 mm.

For some applications, as shown in FIG. 7, a proximal end of sleeve 70 is directly coupled to anchor 20 such that hole 40 of anchor 20 opens directly into the lumen of the sleeve. In other words, the proximal end of the sleeve is coupled to the anchor surrounding the hole. For these applications, treatment device 10 typically does not comprise tether 25. The anchor and sleeve are typically biodegradable, or comprise a plurality of parts that separate over time, allowing the anchor and sleeve to pass through the GI tract.

Figure 8:
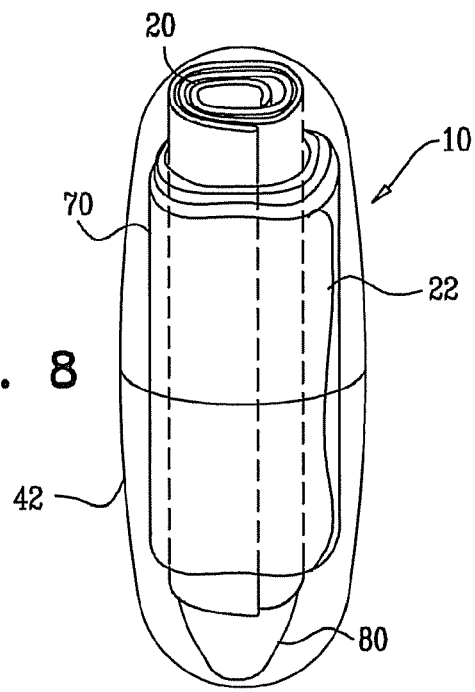
FIG. 8 is a schematic illustration of the device of FIG. 7 in an initial contracted swallowable state, in accordance with an embodiment of the present invention.

Reference is made to FIG. 8, which is a schematic illustration of device 10 in an initial contracted swallowable state, in accordance with an embodiment of the present invention. Before device 10 is swallowed by the subject, sleeve 70 and gastric anchor 20 assume initial contracted positions. For some applications, the sleeve is rolled around the contracted anchor (which, for applications in which the anchor comprises sheet 38, as shown in FIG. 8, is also rolled). Alternatively, sheet 38 is rolled around the sleeve (configuration not shown). As mentioned above, for some applications, device 10 comprises dissolvable enclosure 42 that entirely surrounds device 10 when the device initially assumes its contracted swallowable state, thereby encapsulating or coating the device.

Upon exposure to the contents of the stomach, the sleeve and anchor unroll. Gastric peristalsis moves the sleeve into the duodenum, where duodenal peristalsis extends the sleeve along the duodenum.

For some applications, the distal end of the sleeve is initially shaped to have a rounded tip 80 (e.g., bullet-shaped), which facilitates passage through the pylorus. After passing through the pylorus, the tip dissolves, allowing chyme to pass through the sleeve. Alternatively, for some applications, the distal end of the sleeve comprises a plug that facilitates passage through the pylorus. After the distal end of the sheet with the plug passes through the pylorus, the plug dissolves, allowing chyme to pass through the sleeve. Alternatively, the plug is configured to dissolve more slowly. Duodenal peristalsis naturally pulls the plug more than it pulls the sleeve, thereby causing the plug and distal end of the sleeve to be positioned more distally in the duodenum than is the sleeve. After the sleeve is extended in the duodenum, the plug dissolves.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus comprising:
a swallowable medical treatment device, which is configured to initially assume a contracted state having a volume of less than 4 cm3, and which comprises:
a gastric anchor, which comprises a flexible sheet (a) which initially is rolled to assume a contracted size, (b) which is configured to, upon coming in contact with a liquid, unroll to assume an expanded size that is sufficient to prevent passage of the anchor through a round opening having a diameter of between 1 cm and 3 cm, and (c) which is shaped so as to define a hole therethrough having a radius of at least 0.4 cm;

a medical treatment component, which is coupled to the gastric anchor; and
a dissolvable enclosure, which surrounds the gastric anchor and the medical treatment component when the device initially assumes the swallowable contracted state.

2. The apparatus according to claim 1, wherein the treatment component comprises a drug.

3. The apparatus according to claim 1, wherein the treatment component comprises an electrical stimulator.

4. The apparatus according to claim 1,
wherein the opening is a pylorus of a subject,
wherein the liquid is stomach contents of the subject,
wherein the gastric anchor is configured to, upon coming in contact with the stomach contents, unroll to assume the expanded size that is sufficient to prevent passage of the anchor through the pylorus, and
wherein the hole is sized to allow chyme to pass to the pylorus.

5. A method comprising:
receiving, by a subject, a swallowable treatment device in an initially contracted state, which includes (i) a gastric anchor, which includes a flexible sheet (a) which initially is rolled to assume a contracted size, (b) which is configured to, upon coming in contact with a liquid, unroll to assume an expanded size that is sufficient to prevent passage of the anchor through a round opening having a diameter of between 1 cm and 3 cm, and (c) which is shaped so as to define an hole therethrough having a radius of at least 0.4 cm, (ii) a treatment component coupled to the gastric anchor, and (iii) a dissolvable enclosure, which surrounds the gastric anchor and the medical treatment component when the device initially assumes the swallowable contracted state; and
swallowing the treatment device by the subject, so that the dissolvable enclosure dissolves once the swallowable treatment device reaches a stomach of the subject and the anchor, upon coming in contact with stomach contents of the subject, unrolls sufficiently to prevent passage of the anchor through a pylorus of the subject, and to allow chyme to pass through the hole to the pylorus.

6. The method according to claim 5, wherein the treatment component includes a drug, and wherein receiving comprises receiving the treatment device including the gastric anchor and the drug.

7. The method according to claim 5, wherein the treatment component includes a gastric electrical stimulator, and wherein receiving comprises receiving the treatment device including the gastric anchor and the gastric electrical stimulator.

8. The method according to claim 7, wherein the gastric electrical stimulator is configured to apply electrical stimulation to the stomach, and to configure the stimulation to generate peristalsis.

9. The method according to claim 7, wherein the gastric electrical stimulator is configured to apply electrical stimulation at between 5 and 7 mA, and at a frequency of between 5 and 40 Hz.

10. The method according to claim 5, wherein the medical treatment device further includes one or more dissolvable elements, and wherein swallowing comprises swallowing the treatment device while the one or more dissolvable elements initially hold the sheet rolled.

11. The method according to claim 10, wherein the one or more dissolvable elements include one or more dissolvable rings, and wherein swallowing comprises swallowing the treatment device while the one or more dissolvable rings are initially placed around the rolled sheet.

12. The method according to claim 10, wherein the one or more dissolvable elements include a dissolvable glue, and wherein swallowing comprises swallowing the treatment device while the dissolvable glue binds an outermost edge of the sheet to a more inner portion of the sheet.

13. The method according to claim 10, wherein the one or more dissolvable elements are selected from the group consisting of a dissolvable capsule, and a dissolvable coating, and wherein swallowing comprises swallowing the treatment device while the sheet is within the selected dissolvable element.

14. The apparatus according to claim 3, wherein the electrical stimulator is configured to apply electrical stimulation, and to configure the stimulation to generate peristalsis.

15. The apparatus according to claim 3, wherein the electrical stimulator is configured to apply electrical stimulation at between 5 and 7 mA, and at a frequency of between 5 and 40 Hz.

16. The apparatus according to claim 1, wherein the medical treatment device further comprises one or more dissolvable elements, which initially hold the sheet rolled.

17. The apparatus according to claim 16, wherein the one or more dissolvable elements comprise one or more dissolvable rings, which are initially placed around the rolled sheet.

18. The apparatus according to claim 16, wherein the one or more dissolvable elements comprise a dissolvable glue that initially binds an outermost edge of the sheet to a more inner portion of the sheet.

19. The apparatus according to claim 16, wherein the one or more dissolvable elements are selected from the group consisting of: a dissolvable capsule, and a dissolvable coating.

20. The apparatus according to claim 1, wherein the sheet, when unrolled, has a length of between 20 and 40 mm, and a width of between 10 and 30 mm.

21. The apparatus according to claim 1, wherein the sheet and the hole are coplanar when the sheet is unrolled and otherwise unconstrained.

22. The apparatus according to claim 1, wherein the sheet initially is rolled into a cylinder with portions of the sheet overlapping each other.

23. The apparatus according to claim 1, wherein the sheet is shaped so as to define the hole therethrough having the radius of at least 0.4 cm both when the sheet is rolled and when the sheet is unrolled.

24. The apparatus according to claim 1, wherein the sheet is generally flat when unrolled and otherwise unconstrained.

25. The apparatus according to claim 1, wherein the sheet has exactly external one border when unrolled.

26. The apparatus according to claim 1, wherein the medical treatment component comprises a duodenal unit, which is configured to pass through the opening, and which is coupled to the gastric anchor such that the duodenal unit is held between 1 cm and 20 cm from the gastric anchor.

27. The apparatus according to claim 26, wherein the swallowable medical treatment device further comprises a tether, which couples the duodenal unit to the gastric anchor, and has a length of between 1 cm and 20 cm.

28. The apparatus according to claim 26, wherein the flexible sheet is initially rolled around at least a portion of the duodenal unit.

29. The method according to claim 5, wherein the sheet and the hole are coplanar when the sheet is unrolled and otherwise unconstrained.

30. The method according to claim 5, wherein receiving the swallowable treatment device comprises receiving the swallowable treatment device when the sheet initially is rolled into a cylinder with portions of the sheet overlapping each other.

31. The method according to claim 5, wherein the sheet is shaped so as to define the hole therethrough having the radius of at least 0.4 cm both when the sheet is rolled and when the sheet is unrolled.

32. The method according to claim 5, wherein the sheet is generally flat when unrolled and otherwise unconstrained.

33. The method according to claim 5, wherein the sheet has exactly external one border when unrolled.

34. The method according to claim 5, wherein the medical treatment component includes a duodenal unit, which is configured to pass through the opening, and which is coupled to the gastric anchor such that the duodenal unit is held between 1 cm and 20 cm from the gastric anchor.

35. The method according to claim 34, wherein the swallowable medical treatment device further includes a tether, which couples the duodenal unit to the gastric anchor, and has a length of between 1 cm and 20 cm.

36. The method according to claim 34, wherein receiving the swallowable treatment device comprises receiving the swallowable treatment device when the flexible sheet is initially rolled around at least a portion of the duodenal unit.

* * * * *